(12) United States Patent
Höge (10) Patent No.: US 8,533,131 B2
(45) Date of Patent: Sep. 10, 2013

(54) METHOD AND DEVICE FOR CLASSIFICATION OF SOUND-GENERATING PROCESSES

(75) Inventor: Harald Höge, Gauting (DE)

(73) Assignee: Siemens Aktiengesellschaft, Munich (DE)

( * ) Notice: Subject to any disclaimer, the term of this patent is extended or adjusted under 35 U.S.C. 154(b) by 391 days.

(21) Appl. No.: 12/736,753

(22) PCT Filed: Mar. 12, 2009

(86) PCT No.: PCT/EP2009/052938
§ 371 (c)(1),
(2), (4) Date: Nov. 5, 2010

(87) PCT Pub. No.: WO2009/135719
PCT Pub. Date: Nov. 12, 2009

(65) Prior Publication Data
US 2011/0060564 A1    Mar. 10, 2011

(30) Foreign Application Priority Data
May 5, 2008    (DE) ......................... 10 2008 022 125

(51) Int. Cl.
G06F 15/18    (2006.01)

(52) U.S. Cl.
USPC ........................................................ 706/12

(58) Field of Classification Search
USPC ......................................... 706/12, 45, 47, 62
See application file for complete search history.

(56) References Cited

U.S. PATENT DOCUMENTS

| | | | |
|---|---|---|---|
| 5,602,761 A | | 2/1997 | Spoerre et al. |
| 5,675,497 A | * | 10/1997 | Petsche et al. ................ 702/182 |
| 6,006,170 A | * | 12/1999 | Marcantonio et al. ........ 702/182 |
| 6,227,036 B1 | | 5/2001 | Yonak et al. |
| 6,591,226 B1 | * | 7/2003 | Hartmann et al. ............ 702/183 |
| 2002/0013664 A1 | * | 1/2002 | Strackeljan et al. ............ 702/34 |
| 2005/0059046 A1 | * | 3/2005 | LaBrenz et al. .................. 435/6 |

(Continued)

FOREIGN PATENT DOCUMENTS

| | | |
|---|---|---|
| DE | 4207728 A1 | 9/1993 |
| DE | 102004023824 A1 | 12/2005 |

(Continued)

OTHER PUBLICATIONS

Yang et al., A Study on Retrospective and Online Event Detection, 1998, ACM, pp. 28-36.*
Fraley et al. How Many Clusters? Which Clustering Method? ANswers Via Model-Based Cluster Analysis, 1998, THe COmputer Journal, pp. 1-11.*

(Continued)

*Primary Examiner* — David Vincent
(74) *Attorney, Agent, or Firm* — Staas & Halsey LLP (57) ABSTRACT

Sound-generating processes are classified using at least one sensor for detecting sound signals caused by the sound-generating processes. A storage stores a reference model which has statistical distribution parameters for predetermined characteristics of a sound signal. An adaptation unit extracts the characteristic from the detected sound signals of the processes and calculates a similarity between the sound signals detected based on the extracted characteristics for grouping the processes into various process clusters having sound signals that are similar to each other. The adaptation unit adapts the stored reference model as a function of the statistical distribution parameters of those processes in a process cluster having the maximum number of processes, then a classification unit classifies the sound-generating processes based on the adapted model.

20 Claims, 8 Drawing Sheets

(56) References Cited

U.S. PATENT DOCUMENTS

| | | | |
|---|---|---|---|
| 2007/0100623 A1 | 5/2007 | Hentschel et al. | |
| 2007/0291958 A1* | 12/2007 | Jehan | 381/103 |
| 2008/0069366 A1 | 3/2008 | Soulodre | |
| 2008/0144927 A1* | 6/2008 | Hashimoto et al. | 382/156 |
| 2009/0115635 A1 | 5/2009 | Berger et al. | |

FOREIGN PATENT DOCUMENTS

| | | |
|---|---|---|
| DE | 102008022125.2 | 5/2008 |
| DE | 102006056106 A9 | 9/2008 |
| EP | 0371631 A2 | 6/1990 |
| EP | 1 307 833 B1 | 6/2006 |
| EP | 1 813 921 A1 | 8/2007 |
| WO | 99/54703 | 10/1999 |

OTHER PUBLICATIONS

S. Huebner; "DSPRolog: Quick Reference"; Version 1.1; Apr. 2007; printed from tocsy.agnid.uni-potsdam.de/DSProlog/Manual.pdf; pp. 1-47.

S. Hübner; "Wissensbasierte Modellierung von Audio-Signal-Kassifikatoren"; Zur Bioakustik von *Tursiops truncatus*; printed from opus.kobv.de/ubp/volltexte/2008/1663; Dissertation, Potsdam University; Aug. 2006; pp. 1-209.

Communication from European Patent Office mailed Aug. 12, 2010 for Application No. PCT/EP2009/052938.

International Search Report for Application No. PCT/EP2009/052938; mailed Jun. 4, 2009.

* cited by examiner

METHOD AND DEVICE FOR CLASSIFICATION OF SOUND-GENERATING PROCESSES

CROSS REFERENCE TO RELATED APPLICATIONS

This application is the U.S. national stage of International Application No. PCT/EP2009/052938, filed Mar. 12, 2009 and claims the benefit thereof. The International Application claims the benefits of German Application No. 102008022125.2 filed on May 5, 2008, both applications are incorporated by reference herein in their entirety.

BACKGROUND

Described below are a method and a device for classification of sound-generating processes, of sound signals which are generated for operating processes of a machine or for chemical processes of a system for example.

In most processes sound or vibration signals are generated which characterize the processes. For example gas bubbles can arise during chemical processes which give rise to sounds in the tank facilities or in pipes. Machines or machine components which in a manufacturing or production process generate characteristic sounds or vibration signals as a function of their operating status and possibly their environmental conditions represent a further example.

The analysis of measurement data of technical processes is used for purposes such as uncovering defective components. The analysis of measurement data, especially of sound-generating processes, can be undertaken by physical models or by statistical models of the respective process. These models are created as a rule at a prototype process under laboratory conditions and are used in the field, when the device is being used in a production shop for example. In such situations it can occur that the measurement data, which is obtained on the basis of sound-generating processes, is influenced by changing environmental signals, for example because of changes in room acoustics. It can also occur that the machine being investigated or the process being investigated is operating under other operating conditions or with modified machine components. If the physical or statistical models obtained from a prototype of a process are used unchanged in the field, the quality of the analysis can fall so far that no satisfactory classification of the investigated process or of the investigated machine can be achieved. Typically a defective machine part will not be correctly classified as faulty.

Thus the physical or statistical models of the process to be investigated are adapted to the changing conditions in order to guarantee a sufficient quality of analysis. If for example an operating process of a machine part is investigated, a specific characteristic of the detected sound signal can be included for classification on the basis of the sound signal generated by the machine part. A possible characteristic of the sound signal is the volume of the sound signal or of the noise signal. If the volume of the sound signal exceeds a predeterminable threshold, the investigated machine part is classified as defective and a corresponding error is signaled. If however the environmental conditions change, for example because of an additional device sited next to the machine part, for example a fan, which generates an additional noise signal, the volume level or the preselected threshold will be exceeded and a fault-free machine part will be mistakenly classified as faulty. Thus in a known method of operation setting a meaningful threshold value or classification criterion is complex and time-intensive, since under some circumstances noise signals from defective machine parts which are installed as extra parts in the machine for the purpose, must also be measured to set a suitable threshold value. A further disadvantage of this known method of operation lies in that fact that, when the environmental signals change rapidly, a necessary adaptation of the physical and statistical models often occurs too slowly, so that the necessary quality of the analysis cannot be obtained in good time.

SUMMARY

An aspect is to classify sound-generating processes by carrying out a model adaptation automatically with little computing effort and to guarantee a fault-free classification of sound-generating processes even if environmental conditions are changing rapidly.

The method classifies sound-generating processes with the following:
  Detection of sound signals which are generated by the sound-generating processes,
  Extraction of predetermined characteristics from the detected sound signals for the respective sound-generating process,
  Computing a similarity between the detected sound signals on the basis of the extracted characteristics for grouping processes with sound signals similar to one another into process clusters,
  Adapting statistical distribution parameters of a reference model as a function of the statistical distribution parameters of those processes which are contained in the process cluster with the highest number of processes grouped within it, for creating an adapted model,
  Classifying the sound-generating processes based on the adapted model.

In an embodiment, the sound signal is generated by a working process of a machine.

In an embodiment, the sound signal is generated by a chemical process of a system.

In an embodiment, the sound signal is formed by an airborne sound signal or by a body sound signal.

In an embodiment, the detected sound signal is converted by a sensor into an electric signal.

In an embodiment, the detected electric sound signal is lowpass filtered.

In an embodiment, the analog sound signal is converted into a digital sound signal by an analog-to-digital converter.

In an embodiment, predetermined time windows of the digitized sound signal are subjected to a frequency transformation for creating a sound signal spectrum.

In an embodiment, characteristics of the sound signal are extracted from the time range of from the frequency range.

In an embodiment, feature vectors which exhibit the extracted characteristics are formed for each sound-generating process at different measurement times.

In an embodiment, statistical distribution parameters are computed for each characteristic from a number of characteristic vectors of a process.

In an embodiment the statistical distribution parameters of a characteristic have an average value and a variance of the respective characteristic.

In an embodiment, a distance between the statistical distribution parameters of different sound signals is computed to determine a similarity between the sound signals.

In an embodiment, sound signals similar to one another of processes of which the statistical distribution parameters are at a short distance from one another are grouped into a process cluster.

In an embodiment, the statistical distribution parameters of the reference model are computed on the basis of extracted characteristics of a sound signal which is emitted by a prototype.

In an embodiment, the number of processes within the differently formed process clusters is determined.

In an embodiment, that process cluster is selected of which the number of processes grouped within it is at a maximum.

In an embodiment, the classification of the sound-generating processes is undertaken on the basis of an adapted model by a maximum-likelihood method.

A device for classification of sound-generating processes includes:
at least one sensor for detecting sound signals which are generated by the sound-generating processes,
a memory for storing a reference model having statistical distribution parameters for predetermined characteristics of a sound signal,
an adaption unit for extracting the characteristics from the detected sound signals of the processes and for calculating a similarity between the detected sound signals on the basis of the extracted characteristics for grouping the processes into different process clusters with sound signals similar to one another,
with the adaptation unit adapting the stored reference model as a function of statistical distribution parameters of those processes which are contained in the process cluster with the maximum number of processes,
and with a classification unit which classifies the sound-generating processes based on the adapted model.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Reference will now be made in detail to the preferred embodiments, examples of which are illustrated in the accompanying drawings, wherein like reference numerals refer to like elements throughout.

Figure 1:
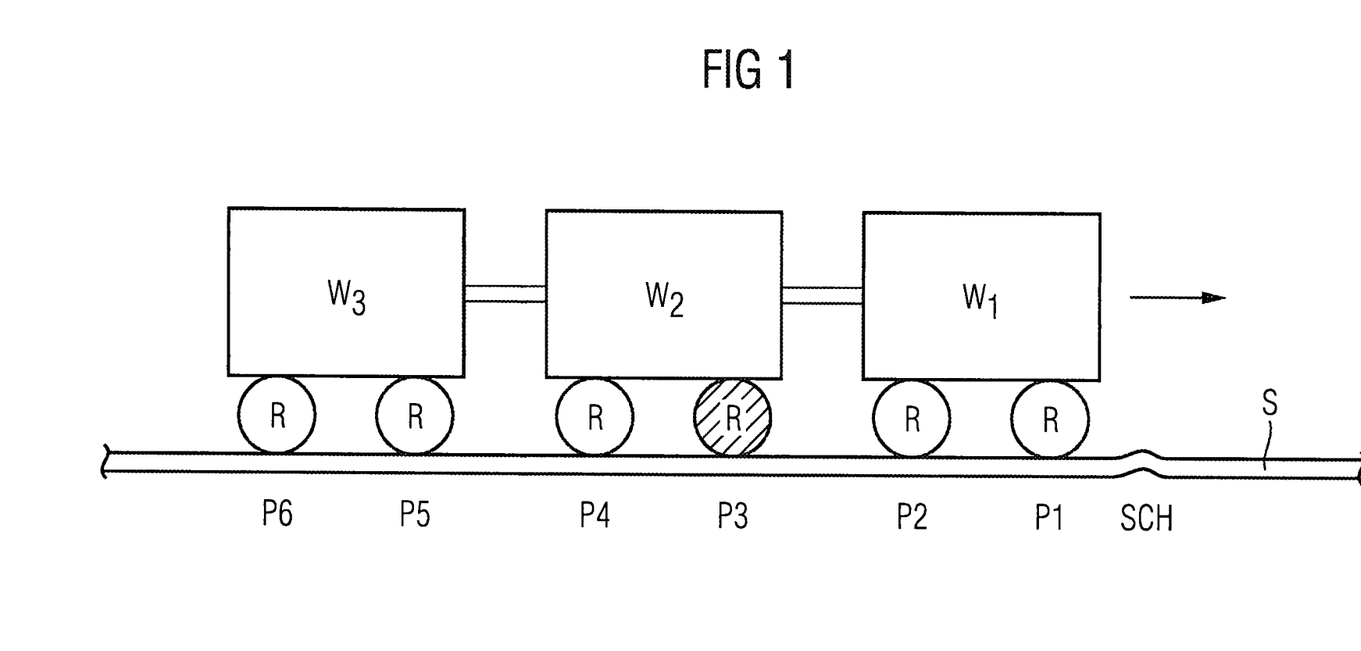
FIG. 1 is a block diagram of a simple exemplary embodiment of the method.

A simple exemplary embodiment for the method for classification of sound-generating processes is shown in FIG. 1. A number of wagons W of a train are moving on a rail S. The wagons W run on wheels R which during the rolling process generate a sound signal because of the friction. The sound signal features airborne sound on the one hand and body sound on the other hand. If the wheels R run over an elevation or threshold of the rail, the amplitude of the sound signal increases. In the example shown the front wheel of the second wagon W2 is detective. This defective wheel or this detective machine part generates a different sound signal from the usual non-defective wheels of the train. With the method it is possible to classify a machine part defective in this way as faulty. In the simple exemplary embodiment shown in FIG. 6 the sound-generating processes of various similar machine parts are classified. In the example given the process is a sound-generating working process. The method is however suitable for any type of processes in which a sound signal or a vibration signal is generated. For example sound-generating chemical processes can also be classified, in which for example gases arise which give rise to sound or vibration signals in pipes or in tank facilities.

Figure 2:
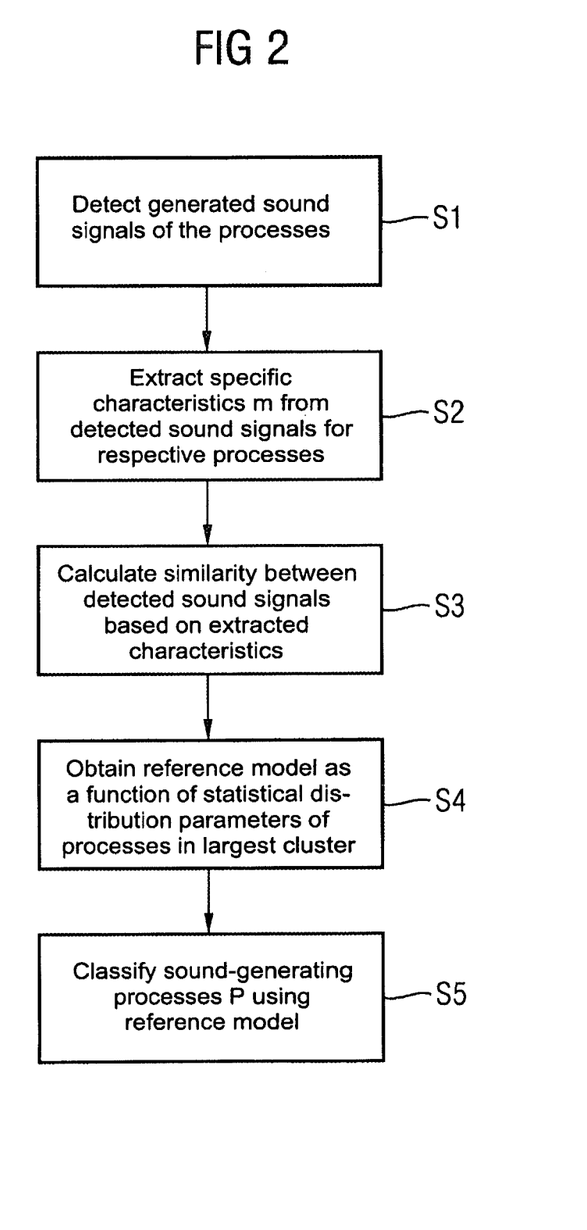
FIG. 2 is a flow diagram of a possible form of embodiment of the method for classifying sound-generating processes.

FIG. 2 shows a flow diagram of a possible form of embodiment of the method for classification of sound-generating processes.

In S1 generated sound signals of the processes, for example the sound-generating processes which are produced by the six wheels shown in FIG. 1, are detected. The sound signals are typically detected by sound pickups or vibration sensors which are located in the vicinity of the location at which the sound-generating process P is running.

In S2 specific characteristics m are extracted from the detected sound signals for the respective process P. A sound signal can feature a plurality of different characteristics m. One possible characteristic m is the volume or the sound level of the signal for example. Further possible characteristics are amplitudes or signal levels at different frequencies, especially modulation frequencies. These frequencies can be predetermined for example by a rotational frequency $f_{rot}$ of a rotating or a turning body. In the simple exemplary embodiment shown in FIG. 1 a possible characteristic m is the amplitude A(f) of the sound signal at the rotational frequency $f_{rot}$ of the wheels R. If for example there is a defect in the rolling surface of wheel R on the radius at one point, this causes a characteristic change in the sound signal during each full rotation of the wheel. The number of predetermined characteristics m can vary. For example 10 to 500 characteristics m of the sound signal can be predetermined. These different characteristics m form a characteristic vector V of the sound signal.

In S3, a similarity between the detected sound signals is computed on the basis of the extracted characteristics for grouping processes with sound signals similar to one another into process clusters C. In this case for example a distance A or a space between the characteristic vectors V in a multi-dimensional vector space is computed.

In S4 statistical distribution parameters of a reference model are adapted as a function of the statistical distribution parameters of those processes P which are contained in that process cluster C having the highest number of processes grouped within it.

The reference model adapted in S4 is used in S5 for classifying the sound-generating processes P. The classification in S5 can typically be undertaken by a maximum-likelihood algorithm.

Figure 3:
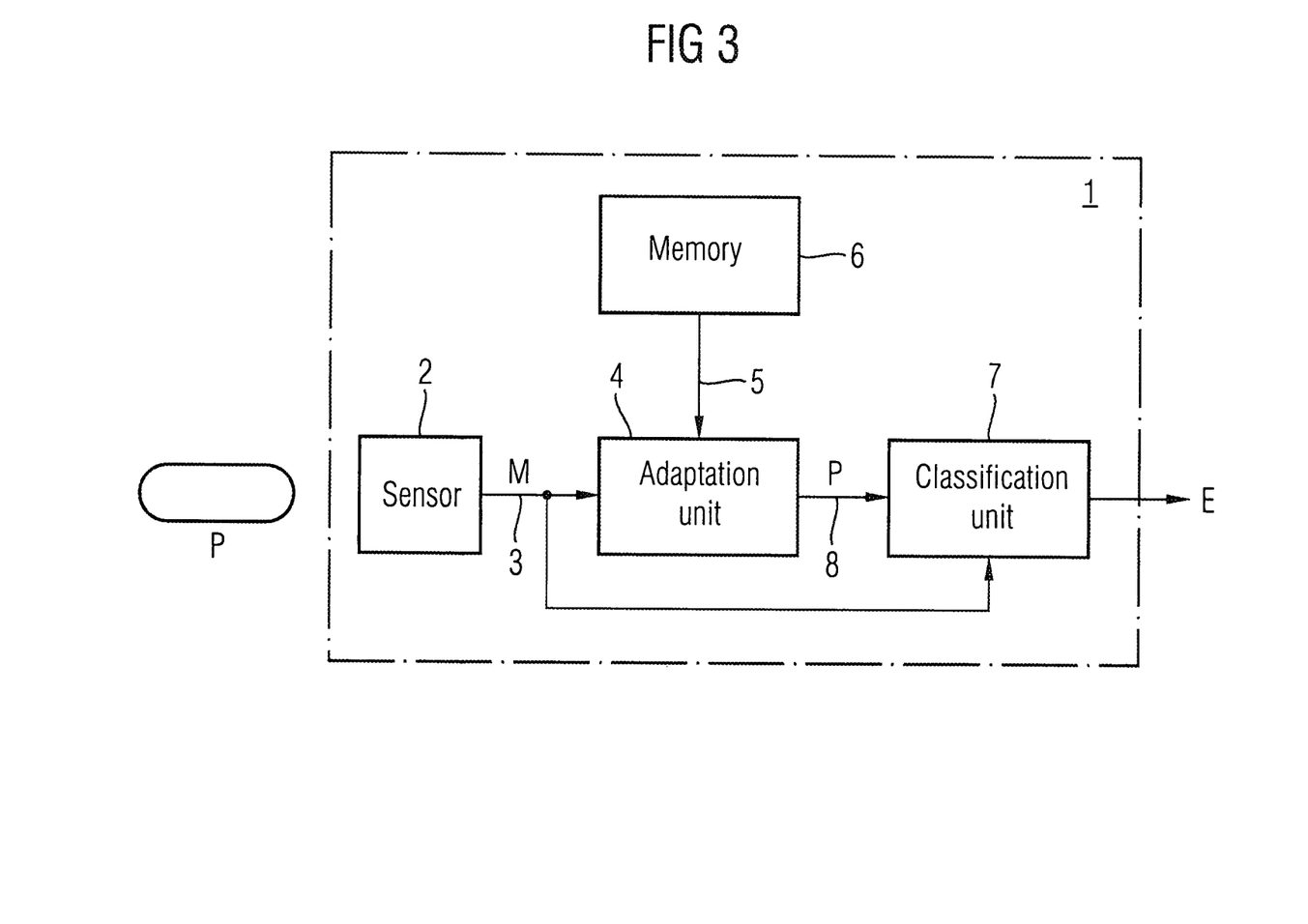
FIG. 3 is a block diagram of an exemplary embodiment of a device for classification of sound-generating processes.

FIG. 3 shows an exemplary embodiment of a device for classification of sound-generating processes. The device 1 features at least one sensor 2 for detecting sound or vibration signals which are generated by a sound-generating process P. The sensor 2 is typically a microphone for detecting a sound signal. In an alternate form of embodiment the sensor 2 detects a body sound signal and is for example attached to a housing of the machine. In a possible form of embodiment the sensor is an acceleration sensor. The sensor 2 converts the acoustic signal or vibration signal into an electric signal and outputs this as measurement data M over a line 3 to the adaptation unit 4. The adaptation unit 4 extracts specific characteristics m from the detected sound signals of the process P and computes a similarity between the detected sound signals on the basis of the extracted characteristics m. Because of the computed similarity between the sound signals the processes P are grouped into process clusters C which exhibit sound signals similar to one another. The adaptation unit 4 subsequently adapts a reference model, which is read out for example via a line 5 from a memory 6 as a function of statistical distribution parameters of those processes P which are contained in that process cluster C with the maximum number of processes P grouped within it.

A classification unit 7 which is connected via lines 8 to the adaptation unit 4, then classifies the sound-generating processes P based on the model adapted by the adaptation unit 4 and the measurement data M of the processes P.

Figure 4:
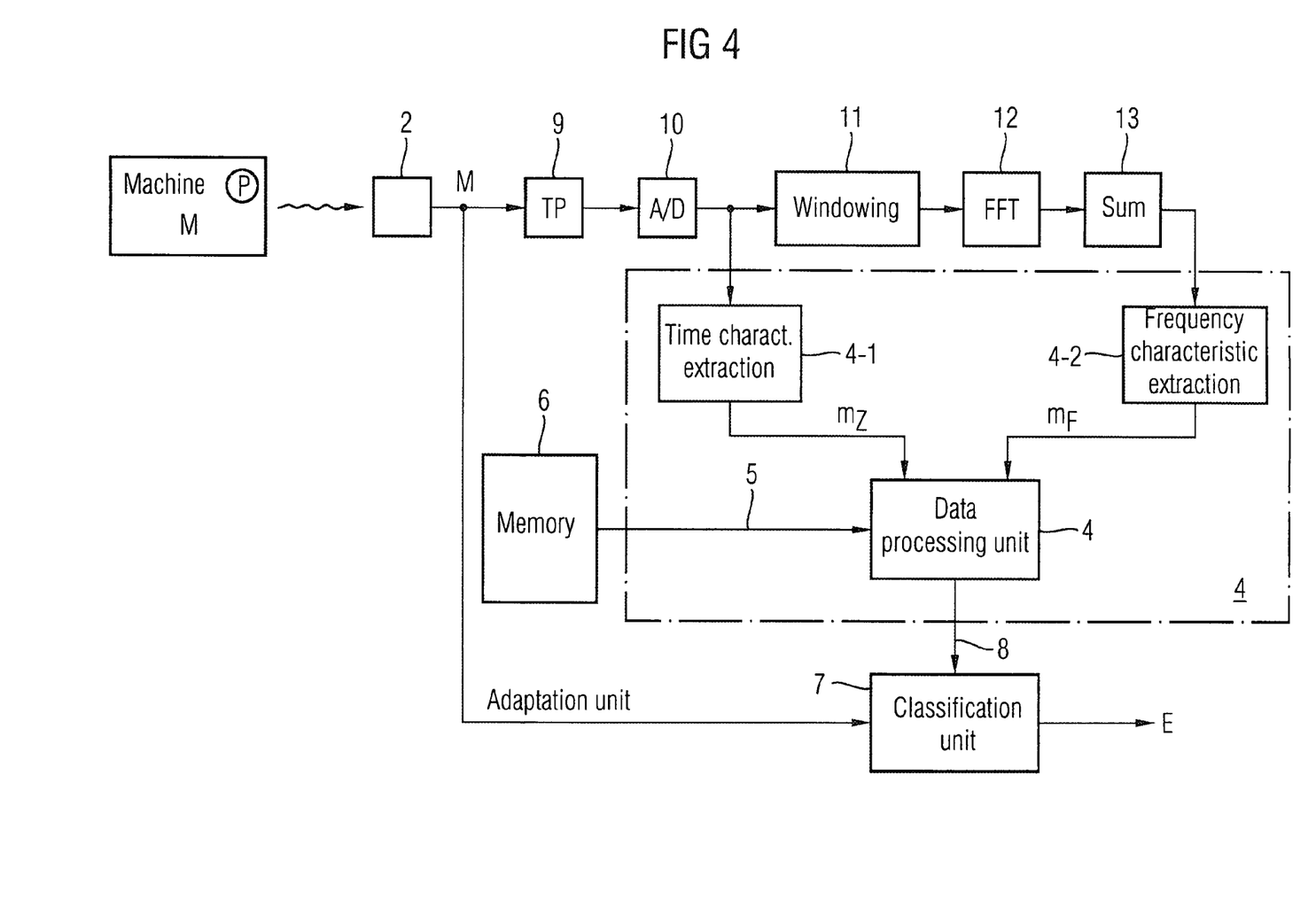
FIG. 4 is a block diagram of an exemplary embodiment of a device for classification of sound-generating processes.

FIG. 4 shows a possible exemplary embodiment of device 1 for classification of sound-generating processes P.

Figure 5A:
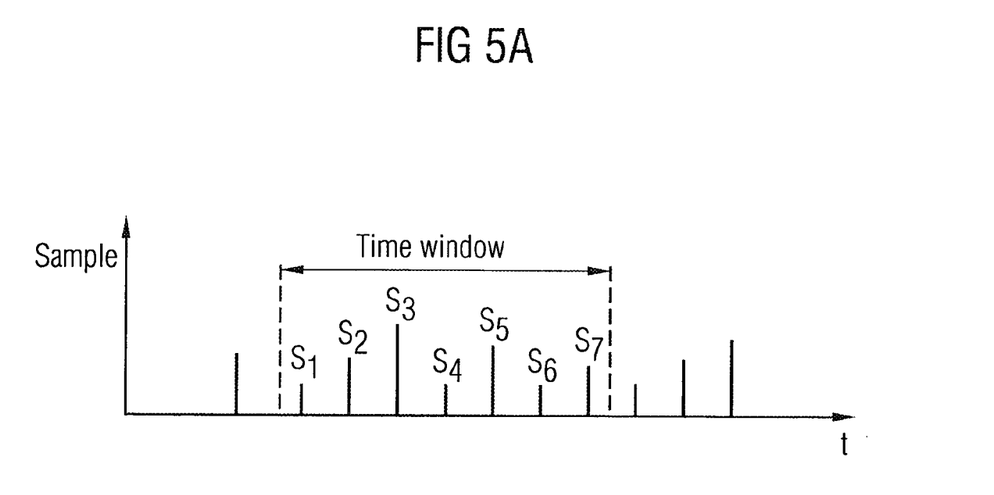
FIGS. 5A and 5B are graphs to illustrate the method for classification of sound-generating processes.
Figure 5B:
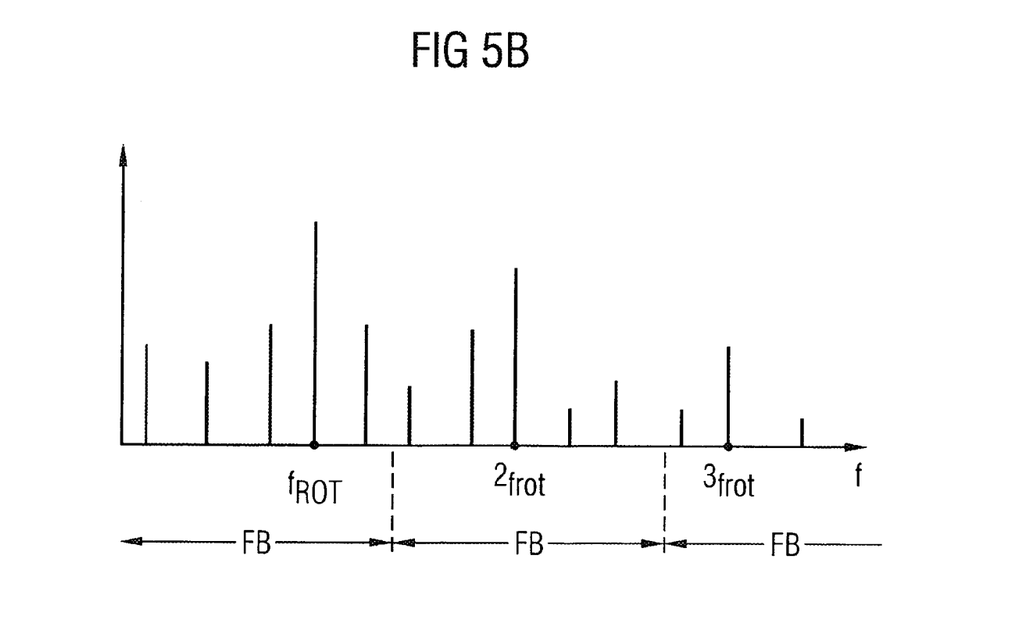

In a machine a sound-generating process P generates a sound or vibration signal which is detected by a microphone 2. The airborne sound signal is converted by the microphone 2 into an electrical signal and is lowpass filtered by a low pass filter 9. The lowpass-filtered signal is sampled by an analog-to-digital converter 10 with a specific sampling frequency and digitized. FIG. 5A shows an example of a digitized sound signal which is output by the analog-to-digital converter 10. A windowing unit 11 forms time windows or segments of the digitized signal. In the example shown in FIG. 5A seven sampling values or samples s1-s7 are output in a time window. The duration of or the extent of the time window may able to be selected. The time window which contains a number of sample values s, is fed to a frequency transformation unit 12. The time window of the digitized sound signal is subjected by the frequency transformation unit 12 to a frequency transformation for creating a sound signal spectrum. For example the windowed sound signal is subjected to a Fast Fourier Transformation FFT in order to form a corresponding sound signal spectrum of the time window. Subsequently a summing unit 13 forms a sum of the sound signal spectrum. FIG. 5B shows an example for a spectrum which is brought about by a rotating body with a specific rotation frequency $f_{rot}$. At the basic frequency $f_{rot}$ and the harmonics the frequency spectrum typically exhibits amplitude maxima.

In the exemplary embodiment shown in FIG. 4 characteristics m of the sound signal are extracted both from the time sound signal and also from the frequency spectrum. To this end the adaptation unit 4 has a unit 4-1 for timer characteristic extraction and a unit 4-2 for frequency characteristic extraction. The characteristics $m_z$ in the time range can for example involve the summed amplitudes of the different samples in the time window or the volume of the sound signal. For the frequency characteristics the amplitudes at the basic frequency $f_{rot}$ and for harmonics, i.e. multiples of the basic frequency, can be evaluated. As an alternative the energy of the signal within a frequency range FB can also be typically included as a characteristic. For each frequency range FB a correspondingly computed energy value which is produced for example from the amplitudes of the spectral components, can be computed. If the spectrum typically has 30 frequency bands, this thus produces 30 different frequency characteristics $m_F$. The characteristics $m_z$ obtained from the time range and the characteristics $m_F$ obtained from the frequency range are supplied to a data-processing unit 4-3 within the adaptation unit 4. The data-processing unit 4 is typically a microprocessor on which a program is running. The data-processing unit 4 loads a stored reference model from the memory 6. The data-processing unit 4 computes, on the basis of the characteristics $m_z$, $m_F$ of the detected sound signals of the processes P, a distance Δ between the detected sound signals in a multidimensional characteristic space, with those processes P which have similar sound signals to one another or for which the computed spaces Δ are small are grouped into a process cluster C. Subsequently the data-processing unit 4 selects that process cluster C which contains the maximum number $Z_{max}$ of processes P. The reference model loaded from the memory 6 is then adapted to the statistical distribution parameters of those processes P which are contained in the largest process cluster C. The classification unit 7 then classifies the sound-generating processes P based on the adapted model. The operating state or fault state determined by the classification unit 7 is output.

Figure 6:
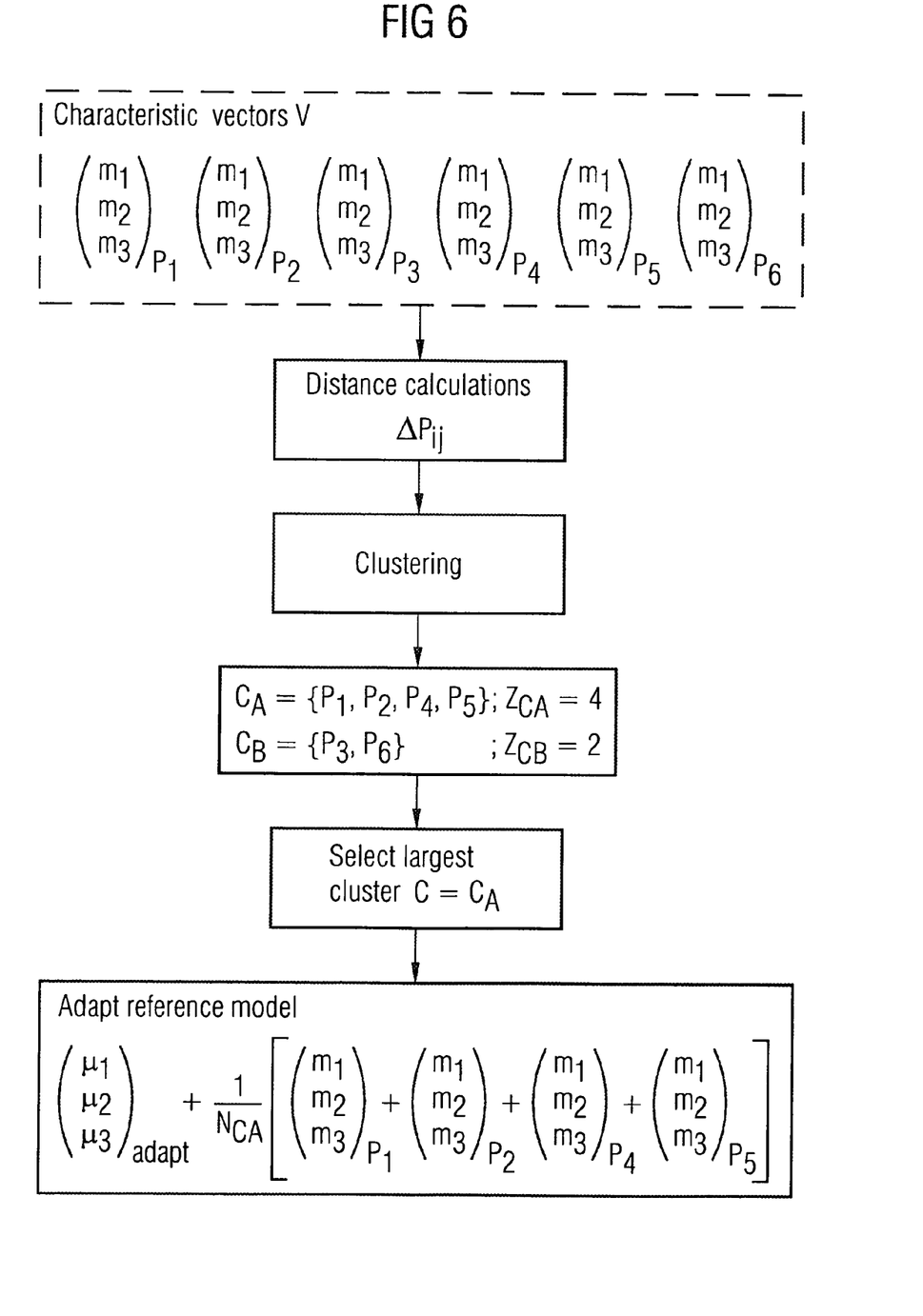
FIG. 6 is a flow diagram of a simple example to illustrate the method for classification of sound-generating processes.

FIG. 6 shows a simple example to illustrate the method. After the detection of the sound signals in S1 specific characteristics m of different processes P are extracted. For example the sound signals of the six different wheels R, as are shown in FIG. 1, are detected. In the simple example shown in FIG. 6 each characteristic vector V has three characteristics m1, m2, m3, for example a signal level of the sound signal as characteristic m1, an amplitude A(f) at a specific frequency f, such as the rotation frequency $f_{rot}$ in FIG. 5B as characteristic m2 and the energy E of the signal in a specific frequency band FB as characteristic m3.

On the basis of the characteristic vectors V of the various processes created P1 through P6 or of the different machine parts a similarity calculation is undertaken. For this purpose distances or spaces between the characteristics m are calculated. For a possible embodiment that various times $t_1$ to $t_M$ the characteristic vectors V for the different processes P are calculated and from them a vector V or a matrix of statistical distribution parameters is calculated.

The following equation illustrates the method of operation.

$$P_1 : \begin{pmatrix} m_1 \\ m_2 \\ m_3 \end{pmatrix}_{t_1} \begin{pmatrix} m_1 \\ m_2 \\ m_3 \end{pmatrix}_{t_2} \cdots \begin{pmatrix} m_1 \\ m_2 \\ m_3 \end{pmatrix}_{t_M} \rightarrow \begin{pmatrix} \mu_1 \\ \mu_2 \\ \mu_3 \end{pmatrix}_{P_1} \quad (1)$$

$$P_2 : \begin{pmatrix} m_1 \\ m_2 \\ m_3 \end{pmatrix}_{t_1} \begin{pmatrix} m_1 \\ m_2 \\ m_3 \end{pmatrix}_{t_2} \cdots \begin{pmatrix} m_1 \\ m_2 \\ m_3 \end{pmatrix}_{t_M} \rightarrow \begin{pmatrix} \mu_1 \\ \mu_2 \\ \mu_3 \end{pmatrix}_{P_2}$$

Figure 7A:
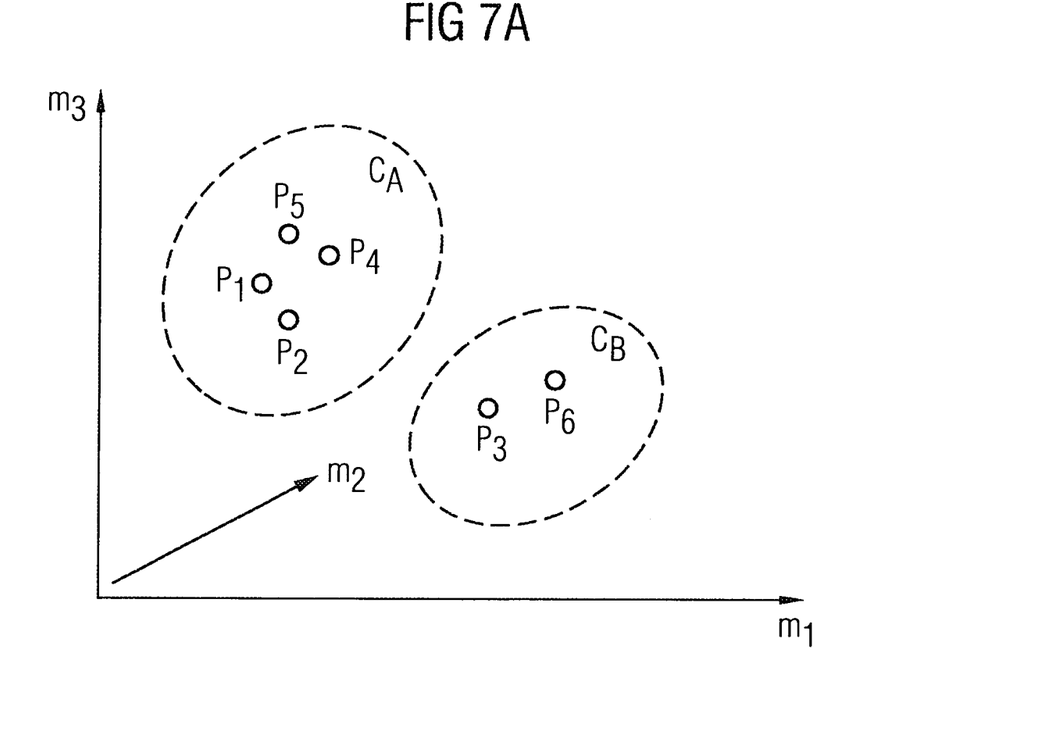
FIGS. 7A and 7B are graphs illustrating the method on the basis of the example shown in FIG. 6.
Figure 7B:
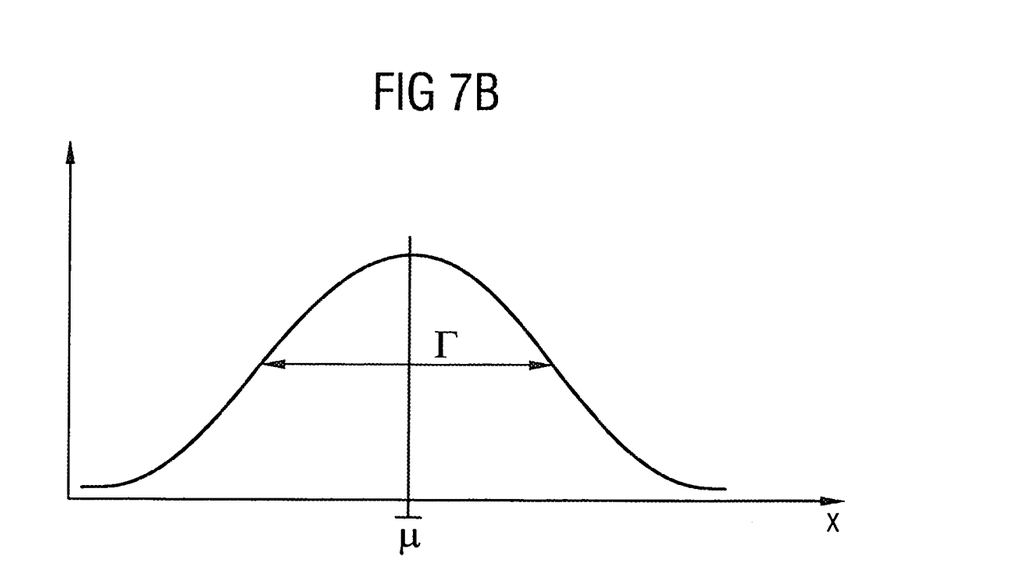

For the specified example the statistical distribution parameter is the average value μ of the characteristic m over a predetermined number of measuring points ti. As well as the statistical distribution parameter average value μ further statistical distribution parameters such as for example the variance σ can be calculated. In this case for example a Gaussian distribution in accordance with FIG. 7B is used as a basis of the statistical distribution. Other statistical distributions with other statistical distribution parameters are also possible.

On the basis of the statistical distribution parameters of the different processes P determined a distance can be calculated in pairs between processes. For example distance Δ between two processes P1, P2 is calculated as follows:

$$\text{Distance}(P_1/P_2) = |\mu_{1p1} - \mu_{1p2}|^2 + |\mu_{1p2} - \mu_{1p2}|^2 + |\mu_{1p3} - \mu_{1p3}|^2 \quad (2).$$

As soon as the similarity between the different sound signals of the different processes P or the distances Δ between the sound signals is calculated on the basis of the statistical distribution parameters, those processes P which have similar sound signals to one another, can be grouped into process clusters. FIG. 7A shows a simple example for the different processes P1-P6 in a three-dimensional characteristic space which is spanned by the characteristics m1, m2, m3. In the example depicted in FIG. 7A the sound signals of the processes P1, P2, P4, P5 are similar to one another and form a cluster $C_A$ while these sound signals or the statistical distribution parameters of the sound signals of processes P3, P6 differ from them and form their own separate process cluster $C_B$. Since the likelihood that the number of non-defective machine components or processes P is greater than the number of machine components or processes that are defective or will become defective, it can be assumed that the sound-generating processes P1, P2, P4, P5 represent the largest clusters $C_A$ of non-defective machine parts. Since the number $Z_A$ of processes P grouped within the process cluster $C_A$ is greater than the number $Z_B$ of the processes P within the process cluster $C_B$ the process cluster $C_A$ will be selected and a reference model of the machine part, as shown in FIG. 6 will be adapted on the basis of the characteristics m of the processes P contained in the process cluster $C_A$. For example the average value μ formed by the average value of the characteristics m of the processes P within the process cluster $C_A$ will be formed as the statistical parameter of a stored reference model. In a possible form of embodiment the adapted reference model is calculated as a function of the statistical distribution parameters of those processes P which are contained in the largest process cluster and as a function of the previous statistical distribution parameters of the reference model. In this form of embodiment the adaptation is thus undertaken in an iterative or evolutionary manner respectively.

Figure 8:
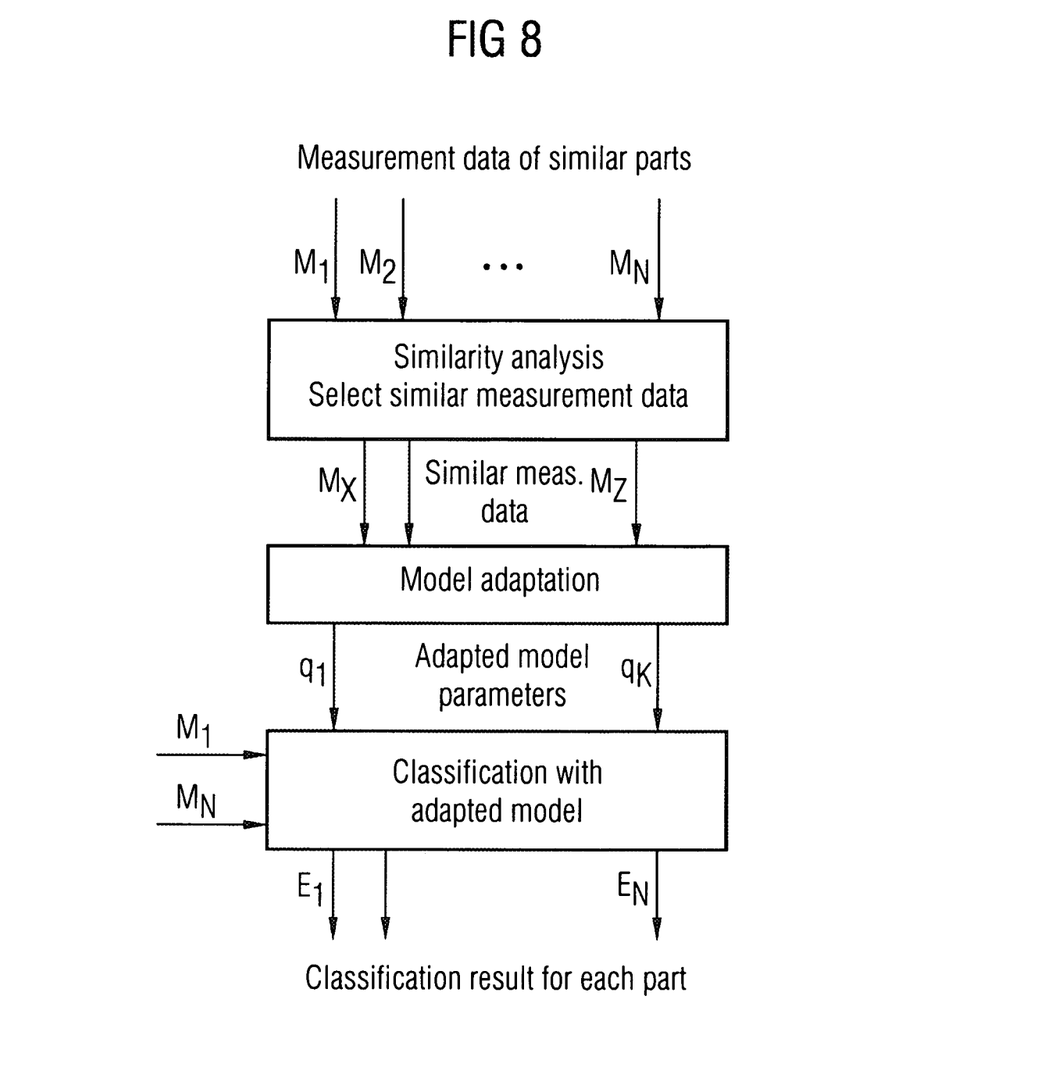
FIG. 8 is a block diagram of an abstract model illustrating the method for classification of sound-generating processes.

FIG. 8 shows an abstract mathematical model for explaining the method. Measurement data M is obtained from different similarly-constructed machine parts, for example the wheels R shown in FIG. 1, which is subjected to a similarity analysis for selecting similar measurement data. The similar measurement data or the sound signals similar to one another are selected and included for model adaptation. A process P is then classified on the basis of the measurement data M of the respective process P and statistical model parameters q of the model. This leads to classification results E which specify for example whether a machine part is defective or not. In such a model adaptation the model parameters q or the statistical distribution parameters respectively, such as the average value μ or the variance a of a statistical distribution, are continuously adapted by similar measurement data M. All measurement signals or measurement data M are classified by the classification unit 7 on the basis of the adapted model. The method makes use of the fact that, for machines into which a number of similar machine parts are installed, most machine parts are not defective and their measurement data can be used for adaptation of the model. The method dispenses with complex adaptation measures for analyzing defective machine parts. In particular it is not necessary with the method to deliberately build in faulty machine parts and carry out a model adaptation on the basis of their noise signals. With the statistical models used in the method the similarity can typically be determined using the logical likelihood scores of the measurement data, with it being able to be deduced from the similarity of the scores whether the measurement data belongs to a non-defective machine part or process or not. Since a number of machine parts are involved in the measurement, if the situation of the data is uncertain, not every measurement value has to be taken into account in the method.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A method of classification of sound-generating processes, comprising:
    detecting sound signals generated by sound-generating processes;
    extracting characteristics from detected sound signals for respective process;
    calculating a similarity between the detected sound signals based on extracted characteristics;
    grouping processes with sound signals similar to each other into process clusters;
    creating an adapted model by adapting statistical distribution parameters of a reference model based on statistical distribution parameters of processes contained in a process cluster with a highest number of processes grouped; and
    classifying the sound-generating processes based on the adapted model.

2. The method as claimed in claim 1, wherein the sound signals are generated by a working process of a machine.

3. The method as claimed in claim 1, wherein the sound signals are generated by a chemical process of a system.

4. The method as claimed in claim 1, wherein the sound signals are formed by an airborne signal or by a body sound signal.

5. The method as claimed in claim 1, further comprising converting the detected sound signals into an electrical signal by a sensor.

6. The method as claimed in claim 1, wherein the detected electrical signal is lowpass filtered by a lowpass filter.

7. The method as claimed in claim 6, further comprising converting an analog sound signal into a digital signal by an analog-to-digital converter.

8. The method as claimed in claim 7, further comprising subjecting predetermined time windows of the digital sound signal to a frequency transformation to create a sound signal spectrum.

9. The method as claimed in claim 8, wherein said extracting the characteristics from detected sound signals includes extracting the characteristics from a time range or from a frequency range.

10. The method as claimed in claim 1, wherein said extracting the characteristics from detected sound signals includes extracting characteristic vectors which have the extracted characteristics formed at different measurement times.

11. The method as claimed in claim 10, further comprising calculating the statistical distribution parameters for each characteristic from characteristic vectors of a process.

12. The method as claimed in claim 11, wherein the statistical distribution parameters of a respective characteristic include an average value and a variance of the respective characteristic.

13. The method as claimed in claim 1, wherein said calculating a similarity between the detected sound signals comprises calculating a distance between the statistical distribution parameters of different sound signals.

14. The method as claimed in claim 13, wherein the statistical distribution parameters of similar sound signals exhibiting a small distance from each other are grouped into a process cluster.

15. The method as claimed in claim 14, wherein said grouping of the processes is determined within differently formed process clusters.

16. The method as claimed in claim 1, further comprising calculating the statistical distribution parameters of the reference model based on the extracted characteristics of a sound signal output by a prototype.

17. The method as claimed in claim 16, further comprising selecting a process cluster for which a number of processes grouped within is largest among all process clusters.

18. The method as claimed in claim 1, wherein said classifying of the sound-generating processes based on the adapted model uses a maximum-likelihood method.

19. A device classifying sound-generating processes, comprising:
at least one sensor detecting sound signals generated by the sound-generating processes;
a memory storing a reference model having statistical distribution parameters for predetermined characteristics of a sound signal;
an adaptation unit extracting characteristics from detected sound signals of the processes, calculating a similarity between the detected sound signals based on the characteristics extracted, grouping the sound-generating processes into different process clusters with similar sound signals, and adapting the reference model as a function of statistical distribution parameters of processes contained in a process cluster having a maximum number of processes; and
a classification unit classifying the sound-generating processes based on the reference model as adapted.

20. A non-transitory computer readable storage embodying a method of classifying sound-generating processes, comprising:
detecting sound signals generated by sound-generating processes;
extracting characteristics from detected sound signals for respective process;
calculating a similarity between the detected sound signals based on extracted characteristics;
grouping processes with sound signals similar to each other into process clusters;
creating an adapted model by adapting statistical distribution parameters of a reference model based on statistical distribution parameters of processes contained in a process cluster with a highest number of processes grouped; and
classifying the sound-generating processes based on the adapted model.

* * * * *